(12) United States Patent
Mickolajczyk et al.

(10) Patent No.: US 9,733,465 B2
(45) Date of Patent: Aug. 15, 2017

(54) WAVEGUIDES FOR ENHANCED TOTAL INTERNAL REFLECTION FLUORESCENCE MICROSCOPY

(71) Applicant: Penn State Research Foundation, University Park, PA (US)

(72) Inventors: Keith Mickolajczyk, University Park, PA (US); Yixin Yan, University Park, PA (US); Yiyang Gong, University Park, PA (US); Haoyu Li, University Park, PA (US); Noel Christopher Giebink, University Park, PA (US); Thomas Jackson, University Park, PA (US); William Hancock, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/041,384

(22) Filed: Feb. 11, 2016

(65) Prior Publication Data
US 2016/0238830 A1     Aug. 18, 2016

Related U.S. Application Data

(60) Provisional application No. 62/115,403, filed on Feb. 12, 2015.

(51) Int. Cl.
*G02B 21/34*     (2006.01)
*G02B 21/16*     (2006.01)
(Continued)

(52) U.S. Cl.
CPC .......... *G02B 21/34* (2013.01); *G01N 21/648* (2013.01); *G01N 21/6458* (2013.01); *G02B 21/16* (2013.01); *G01N 2021/6482* (2013.01); *G02B 6/122* (2013.01); *G02B 6/2726* (2013.01); *G02B 6/29331* (2013.01)

(58) Field of Classification Search
CPC .. G02B 6/122; G02B 6/2726; G02B 6/29331; G02B 6/102; G02B 6/105; G02B 6/2733; G02B 6/2753; G02B 6/276; G02B 21/00; G02B 21/0004; G02B 21/0068; G02B 21/0076; G02B 21/16; G02B 21/34; G02B 21/01
See application file for complete search history.

(56) References Cited

U.S. PATENT DOCUMENTS 6,188,812 B1   2/2001   Kao et al.
6,285,816 B1   9/2001   Anderson et al.
(Continued)

OTHER PUBLICATIONS

Balaa et al., "Surface plasmon enhanced TIRF imaging", Nikon Note 12, 2009.
(Continued)

*Primary Examiner* — John M Bedtelyon
(74) *Attorney, Agent, or Firm* — McDermott Will & Emery LLP

(57) ABSTRACT

Evanescently-coupled planar waveguides for enhancing total internal reflection fluorescence microscopy are disclosed. The waveguides include multiple thin layers of one or more materials on a cover slip arranged resonantly enhance the optical field at the surface of the layer stack by evanescently coupling to a leaky guided mode.

12 Claims, 3 Drawing Sheets

(51) Int. Cl.
*G02B 6/293* (2006.01)
*G02B 6/122* (2006.01)
*G02B 6/27* (2006.01)
*G01N 21/64* (2006.01)

(56) References Cited

U.S. PATENT DOCUMENTS

| | | |
|---|---|---|
| 6,472,671 B1 | 10/2002 | Montagu |
| 7,274,505 B2 * | 9/2007 | Eisenkramer .......... G02B 1/115 359/359 |
| 7,283,707 B1 | 10/2007 | Maleki et al. |
| 7,961,315 B2 | 6/2011 | Cunningham et al. |
| 8,248,599 B2 | 8/2012 | Zhan |
| 8,410,414 B2 | 4/2013 | Wu et al. |
| 8,841,548 B2 | 9/2014 | Giebink et al. |
| 2009/0296200 A1 | 12/2009 | Matsumoto |
| 2011/0129942 A1 | 6/2011 | Ohtsuka |
| 2014/0256561 A1 | 9/2014 | Schwartz et al. |

OTHER PUBLICATIONS

Burghardt et al., "In situ fluorescent protein imaging with metal film-enhanced total internal reflection microscopy", Biophysical Journal 2006:90:4662-4671.

Kaiser et al., "Resonant enhancement of evanescent waves with a thin dielectric waveguide" Optics Communications, 104 (1994) 234-240.

Ke et al., Optimizing the strength of an evanescent wave generated from prism coated with a double-layer thin-film stack, Bioimaging, 5 (1997) 1-8.

Kim et al., "Feasibility study of enhanced total internal reflection fluorescence imaging using dielectric films" Multimodal Biomedical Imaging III, Azar et al. Ed., Proc. of SPIE vol. 6850, 68500R-1 to 68500R-7 (2008).

Kim et al., "Thin-film-based sensitivity enhancement for total internal reflection fluorescence live-cell imaging", Optics Letters, 2007:32(21):3062-3064.

Mickolajczyk et al. "Dielectric planar waveguides for enhanced single-molecule kinesin motility studies in total internal reflection microscopy", Poster displayed Oct. 2014.

* cited by examiner

WAVEGUIDES FOR ENHANCED TOTAL INTERNAL REFLECTION FLUORESCENCE MICROSCOPY

CROSS-REFERENCE TO RELATED APPLICATION

This application claims the benefit of U.S. Provisional Application No. 62/115,403 filed Feb. 12, 2015 the entire disclosure of which is hereby incorporated by reference herein.

STATEMENT REGARDING FEDERALLY SPONSORED RESEARCH

This invention was made with government support under Grant No. GM010067, awarded by the National Institutes of Health. The Government has certain rights in the invention.

TECHNICAL FIELD

The present disclosure relates to total internal reflection fluorescence microscopy and in particular to evanescently-coupled planar waveguides for enhancing such microscopy.

BACKGROUND

A total internal reflection fluorescence microscope (TIRFM) is a type of microscope that allows imaging of a thin region of a specimen which can include living cells. TIRFM exploits the unique properties of an induced evanescent wave or field in a limited specimen region immediately adjacent to the interface between two media having different refractive indices. In practice, the most commonly utilized interface in the application of TIRFM is the contact area between a specimen and a glass cover slip.

The evanescent wave is generated only when the incident light is totally internally reflected at the glass-water interface. The evanescent electromagnetic field decays exponentially from the interface, and thus penetrates to a depth of only approximately 100 to 200 nm into the sample medium. Thus, the TIRFM enables a selective visualization of surface regions such as the basal plasma membrane (which are about 7.5 nm thick) of cells.

Single-molecule TIRF microscopy has been enabled by technical advances in the fields of optics, materials science, and chemistry, and has been adopted as a standard technique in a number of fields. For example, the breakthrough of high quantum yield fluorophores allowed for high precision tracking of single molecular motors in vitro.

Limitations remain, however, in the number of photons that reach the detector from a single fluorophore, ultimately restricting the temporal resolution of imaging experiments. Efforts to enhance TIRFM have been reported. See, e.g., Kim et al., "Thin-film-based sensitivity enhancement for total internal reflection fluorescence live-cell imaging", Optics Letters, 2007:32(21):3062-3064 and Kim et al., "Feasibility study of enhanced total internal reflection fluorescence imaging using dielectric films" Multimodal Biomedical Imaging III, Azar et al. Ed., Proc. of SPIE Vol. 6850, 68500R-1 to 68500R-7 (2008). However, a continuing need exists to enhance fluorescence microscopy.

SUMMARY OF THE DISCLOSURE

An advantage of the present disclosure is a dielectric waveguide for use in total internal reflection fluorescence microscopy.

These and other advantages are satisfied, at least in part, by a cover slip comprising multiple thin layers of one or more dielectric materials on a glass substrate arranged in a planar fashion to couple to a discrete guided mode for resonant enhancement of an evanescent optical field at a surface of the multiple thin layers. For example, the cover slip can include: (i) a coupling layer directly adjacent a glass substrate having a refractive index $n_c$ and a thickness more than about one-half an optical excitation wavelength; and (ii) one or more guide layers on the coupling layer having a refractive index $n_{gi}$ that is more than a medium of a specimen, e.g., a medium of a specimen being imaged. Advantageously, the coupling layer refractive index $n_c$ is less than the one or more guide layers refractive index $n_{gi}$ and the guide layer thicknesses and guide layer refractive indices support a leaky guided mode.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

DETAILED DESCRIPTION OF THE DISCLOSURE

Figure 1:
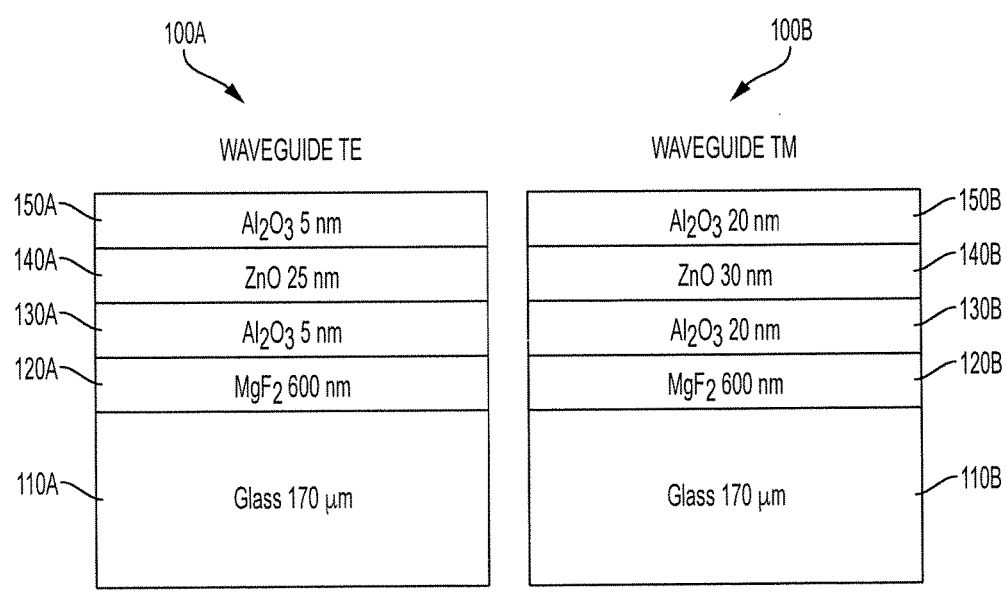
FIG. 1 illustrates examples of the design of the thin films used in the waveguide.

As described in the Background section above, total internal reflection fluorescence microscopy (TIRFM) is limited in the number of photons that reach the detector from a single fluorophore, ultimately restricting the temporal resolution of imaging experiments. To address this problem, a novel dielectric waveguide was designed that can be used in existing commercial TIRF microscopes. A resonance effect along the waveguide lateral direction leads to enhancement of evanescent excitation. Use of the waveguide increases signal intensity from fluorescent probes by over an order of magnitude relative to a standard glass cover slip. The performance of the waveguide is further benchmarked using well-developed single-molecule kinesin motility assays. This technology has broad applications in the growing field of fluorescence microscopy, permitting much greater signals from the same molecular systems without the need for replacing existing microscopy setups.

In TIRFM, a laser beam passes through a high numerical aperture (N.A.) objective and undergoes total internal reflection when reflected from a high-refractive medium (e.g., glass) into a low refractive medium (e.g. cell/water). By using a high N.A. objective, the laser beam can leave the front optical plane of the objective at a supercritical angle to result in total internal reflection. This produces an electromagnetic evanescent wave which penetrates the cell membrane adjacent to the coverglass and excites fluorophores within an ultra thin optical section of about 100 nm, thereby reducing background noise from out-of-focus fluorescence.

In addition to TIRFM, the waveguide architecture is also useful for resonance sensing, in complete analogy to current commercially-available surface plasmon resonance sensors. The advantage of using a dielectric waveguide instead of a metal surface plasmon resonance is that, because the dielectric guide fundamentally enables lower loss than a surface plasmon, the sensitivity of the sensor can be improved, in principle by an arbitrary amount (though in practice limited by surface roughness of the dielectric layers). Surface plasmon resonance (SPR) sensors are widely used to detect everything from viruses to water contaminants. Biosensing Instrument Inc. of Arizona, USA produces commercial SRP instruments.

In one aspect of the present disclosure, evanescent excitation of a TIRFM can be achieved by use of a cover slip, e.g., a glass substrate used to hold a specimen in a medium, which includes multiple thin layers of one or more materials on the covers slip arranged in a planar fashion to create an evanescently-coupled waveguide. A distinguishing characteristic of this architecture is that (i) the refractive index, $n_c$, of the layer adjacent to the glass substrate, herein referred to as the 'coupling layer' should be lower than the refractive indices of all subsequent layers, (ii) a thickness of the coupling layer should be greater than approximately one-half of an optical excitation wavelength, (iii) a refractive index, $n_{gi}$, of the one or more layers deposited on top of the coupling layer, herein referred to as the 'guide layer(s)' should exceed that of a medium of a specimen being imaged, i.e., the coverslip ambient (typically an aqueous medium with n~1.33), (iv) the uppermost guide layer is preferably physically stable (i.e. not dissolve) in the ambient solution and (v) the combination of guide layer thicknesses and refractive indices must support a leaky guided mode.

For example, the multiple guide layers with high refractive index can have a refractive index of between 1.5 and 4.0. The coupling layer can have a low refractive index of between 1.0 and 1.5. The optical excitation wavelength typically ranges between 300-700 nm, the coupling layer thickness typically exceeds 600 nm, and the collective thicknesses of the guide layers typically exceed 20 nm, for example.

In one aspect of the present disclosure, the high refractive index layer can include one or more dielectric materials such as $TiO_2$, $ZnO$, $Al_2O_3$, $TeO_2$, SiNx, conjugated polymers, chalcogenide glasses (and many others), and the low index materials can include $MgF_2$, $CaF_2$, PTFE/Teflon, nanoporous silicates/aerogels (and many others).

Advantageously, the guide layers have a refractive index of between 1.5 and 3 and a thickness range from 10% of the optical excitation wavelength to 10 times the optical excitation wavelength. Typical optical excitation wavelengths range from about 300 nm to about 700 nm. Materials that are useful for the cover slip of the present disclosure include optical glass, such as, for example B270, BK7, SF10 or other high index glasses.

The significance of waveguides being composed entirely of dielectric materials is that they can be entirely transparent to the wavelengths of interest—that is, the materials have little to no absorption at either the excitation or emission wavelengths of interest, between a range of 300 nm and 700 nm. In an embodiment of the present disclosure the guide layers have an absorption coefficient of less than 1 $cm^{-1}$ at wavelengths exceeding 400 nm. This is a fundamental difference relative to surface plasmon-based strategies involving metals, which are inherently absorptive and perform poorly at all wavelengths of interest. The degree to which a resonant structure (such as a waveguide or surface plasmon polariton (SPP)) enhances the optical field is inversely linked to its absorption. Consequently, pure dielectric waveguides can reach higher optical field enhancements than metal-based surface plasmon polariton modes, and thereby enable a large signal increase for TIRFM measurements.

As explained above, the waveguides could also be useful as analogs of SPR-based sensors, with the advantage of improving sensitivity. In this case, the basic architecture remains the same. Such an architecture includes a transparent substrate (macroscopically thick ~1 mm), followed by a thin intermediate layer with low refractive index (less than that of the substrate, typically ranging from n of from about 1.0 to 1.4) and thickness on the order of the emission wavelength, and then subsequently by one or more layers with high refractive index (greater than that of the substrate, typically ranging from n of about 1.6 to about 4.0) and a collective thickness that is again on the order of the optical excitation wavelength. The primary difference for resonance sensing applications is that the top-most layer might be functionalized with, for example, some type of anti-body or agent to bind the target analyte (e.g. a virus) to the film surface.

An example of such a device includes multiple thin layers of dielectric materials deposited in a planar fashion on top of a glass cover slip. The finely tuned thicknesses and indices of refraction of these layers lead to reflection as a function of the incident laser wavelength, angle of incidence, and polarization. Here the layers are designed as so to best amplify the energy passed into the evanescent wave at a designed resonance angle. This leads to better excitation of fluorophores in TIRFM. Additionally, the single evanescent wave that can be made by coupling into the waveguide has physical parameters that are specifically optimized for TIRFM on biological samples. Whereas in conventional TIRFM the initial intensity and penetration depth of the evanescent wave ends up being limited by the numerical aperture of the objective. However, using the waveguide of the present disclosure the optimal evanescent wave can be made by any objective that can reach the coupling angle. The coupling angle is specifically designed to be accessible by many objectives, eliminating the need for expensive, very high numerical aperture objectives in TIRFM.

FIG. 1 illustrates examples of the design of the thin films used in the waveguide of the present disclosure. Two versions of the waveguide are made and tested; one that coupled only transverse electric (TE)-polarized light (100A), and one that coupled only transverse magnetic (TM)-polarized light (100B). These waveguides were made by first thermally evaporating a layer of $MgF_2$ (120A, 120B) over a glass substrate (110A, 110B), followed by plasma-enhanced atomic layer deposition of $Al_2O_3$ (130A, 130B), ZnO (140A, 140B), and $Al_2O_3$ (150A, 150B). The top tri-layer (alumina/ZnO/alumina) is not a necessary combination for optical performance, it could equally well include an all alumina or ZnO layer instead, or any other material with refractive index greater than the $MgF_2$ coupling layer. An advantage of this combination, however, is that it can protect the ZnO from dissolving certain aqueous bio-solutions that can be imaged. For these embodiments, the thicknesses of the layers for the waveguide TE (100A) were 5 nm for $Al_2O_3$ (150A), 25 nm for ZnO (140A), 5 nm for $Al_2O_3$ (130A) and 600 nm for the $MgF_2$ coupling layer (120A). The thicknesses of the layers for the waveguide TM (100B) were 20 nm for Al$_2$O$_3$ (150B), 30 nm for ZnO (140B), 20 nm for Al$_2$O$_3$ (130B) and 600 nm for the MgF$_2$ coupling layer (120B). For both waveguides, the glass substrate had a thickness of 170 microns.

Figure 2:
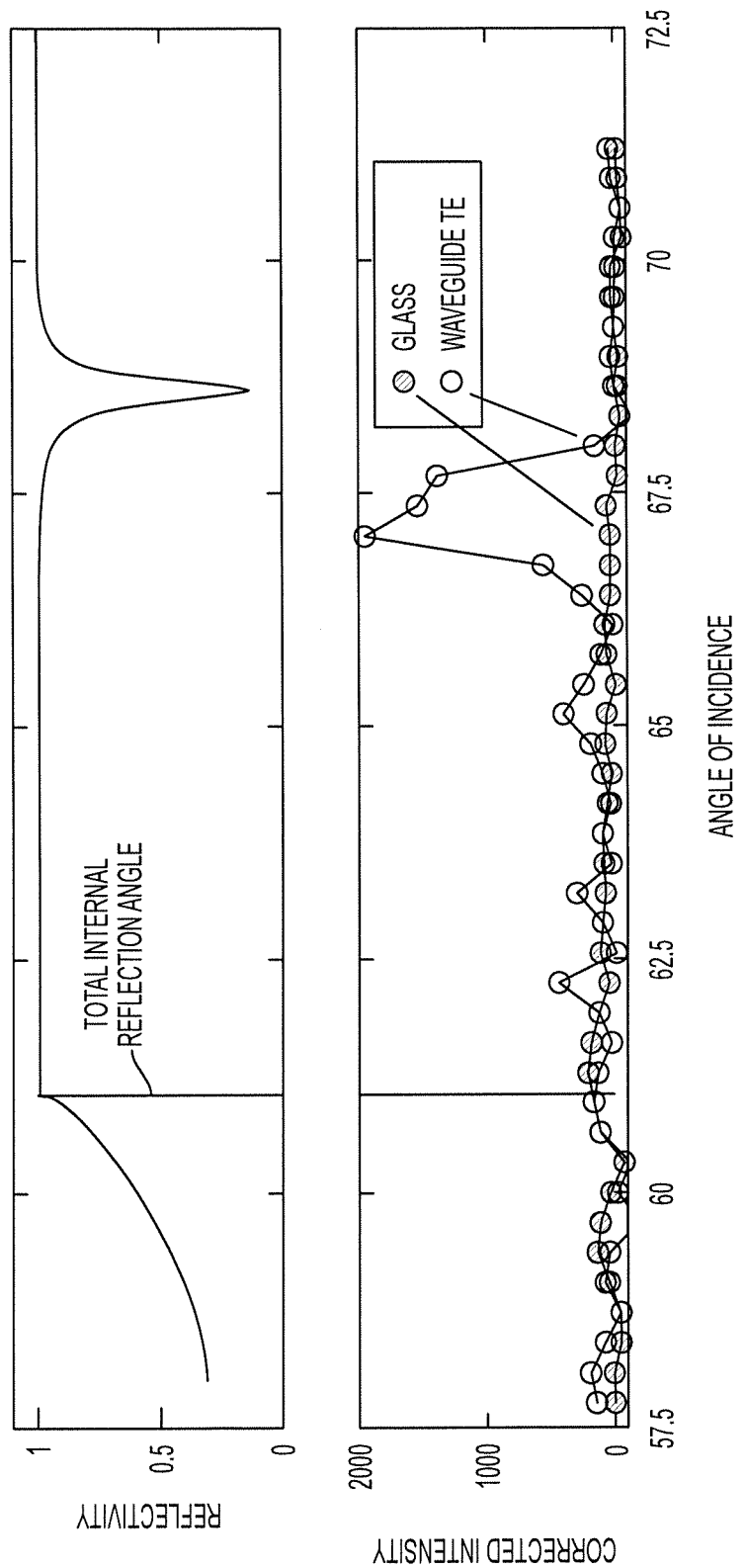
FIG. 2 shows an example angle of incidence scan for waveguide TE used in TIRFM.

FIG. 2 shows an example angle of incidence scan for waveguide TE used in TIRFM. The intensity of a fluorescent microsphere is measured as a function of the input light angle of incidence with TE polarization. The top graph shows the resonance angle of the waveguide according to a theoretical model. The bottom graph shows experimental data for the intensity of a fluorescent microsphere as a function of incident light angle. For Regular TIRFM, shown in gray, a slight increase is seen at the critical angle (denoted). For the waveguide (black), a large increase in signal is seen at the coupling angle. The slight discrepancy between the theoretical and experimental resonance angle may be to either error in the measurement of incident angle, or in experimental error in film deposition. This data show that an enhancement in total signal of well over an order of magnitude is feasible with the waveguides.

Figure 3:
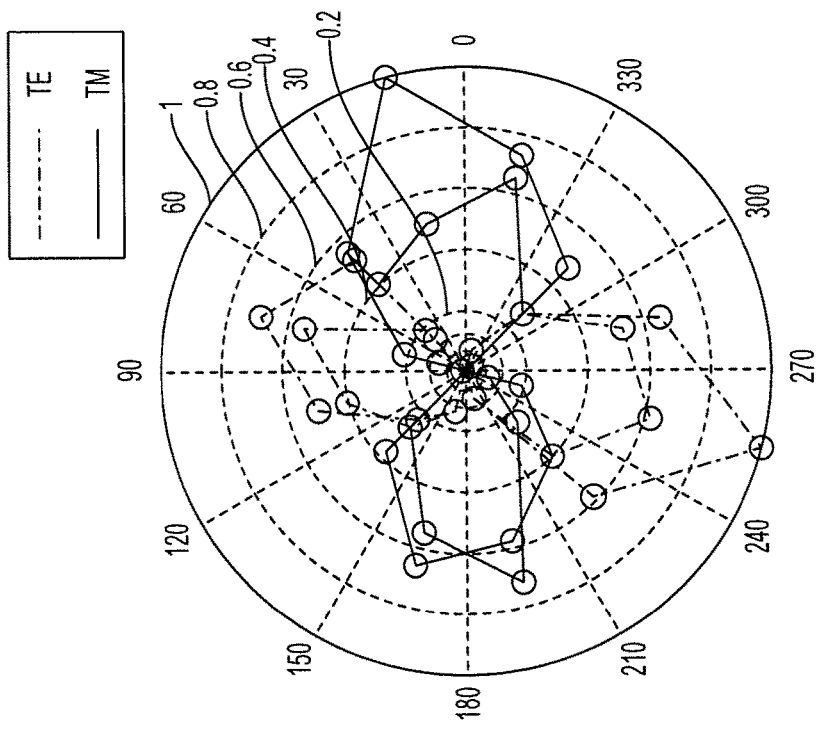
FIG. 3 is an example polarization scan using the waveguides.
Figure 3:
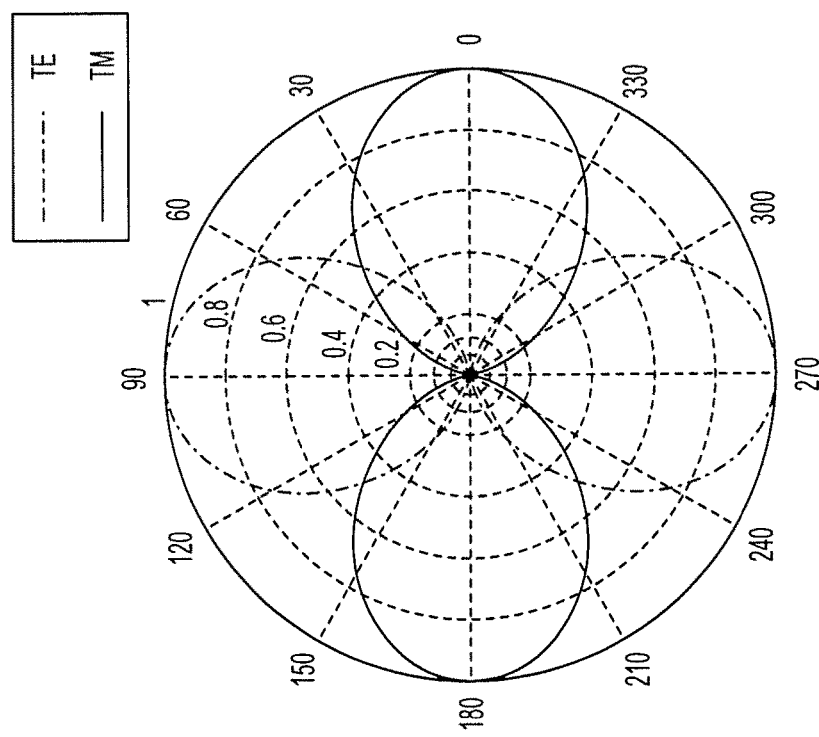

FIG. 3 is an example polarization scan using the waveguides. The left plot shows the theoretical transmission of light through either the TE (gray) or TM (black) waveguide as a function of input light linear polarization angle. The right plot shows the normalized measured intensity (radial axis) of a fluorescent microsphere as a function of incident linear polarization angle. The TE waveguide only couples at TE polarization, and the TM waveguide only couples at TM polarization. Both waveguides transmit no light at the cross-polarization, leading to zero signal from the microspheres. This test benchmarks the successful coupling of the waveguides.

TIRFM is currently limited by the high numerical aperture that must be used. The initial intensity and penetration depth of the evanescent wave used for excitation are both functions of the incident wavelength and angle of incidence, as well as the index of refraction of the glass slide and the biological material (usually close to water, n=1.33). Simply increasing the laser power leads to higher intensity evanescent wave, but also increases the intensity of light >100 nm away from the coverslip, defeating the purpose of the technique. Using a higher index of refraction cover slip can lead to an improved evanescent wave, but requires a higher numerical aperture objective, as the NA must be very close to the cover slip index in order to transmit light. Thus, to improve TIRFM, you must buy as high an NA objective as possible. High performance optics of these types can cost more than $10,000.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

The coverslip waveguides were fabricated by first thermally evaporating a layer of MgF$_2$ on to a cover slip, followed by atomic layer deposition of Al$_2$O$_3$ and ZnO. Other structures were prepared as described above in the detailed Description of the Disclosure.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A cover slip for resonant enhancement of an evanescent optical field, comprising a cover slip having:
   (i) a coupling layer directly adjacent a glass substrate having a refractive index $n_c$, and a thickness more than about one-half an optical excitation wavelength; and
   (ii) one or more guide layers on the coupling layer having a refractive index $n_{gi}$ that is more than a medium of a specimen; wherein $n_c$ is less than refractive indices of any layer subsequent to a coupling layer; and wherein a guide layer thickness and guide layer refractive index support a leaky guided mode.

2. The cover slip of claim 1, wherein each of the one or more guide layers has a refractive index between 1.5 and 4.0.

3. The cover slip claim 1, wherein the coupling layer has a refractive index between 1.0 and 1.5.

4. The cover slip of claim 3, wherein the coupling layer includes one or more of MgF$_2$, CaF$_2$, PTFE/Teflon, or nanoporous silicates/aerogels.

5. The cover slip of claim 1, wherein the collective thickness of the one or more guide layers ranges from 0.1 times the optical excitation wavelength to 10 times the optical excitation wavelength.

6. The cover slip of claim 1, wherein the one or more guide layers include one or more of TiO$_2$, ZnO, Al$_2$O$_3$, TeO$_2$, SiN$_X$, conjugated polymers, or chalcogenide glasses.

7. The cover slip of claim 1, further comprising a specimen thereon wherein the specimen includes a fluorophore.

8. The cover slip of claim 1, wherein the one or more guide layers include one or more of ZnO and/or Al$_2$O$_3$ and the coupling layer includes one or more layers of MgF$_2$.

9. The cover slip of claim 1, wherein the one or more guide layers include a layer of ZnO between two layers of Al$_2$O$_3$ and the coupling layer includes MgF$_2$.

10. The cover slip of claim 1, wherein the optical excitation wavelength ranges between 300-700 nm.

11. The cover slip of claim 1, wherein the one or more guide layers on the coupling layer have $n_{gi}$ that is more than about 1.33.

12. The cover slip of claim 1, wherein the thickness of the coupling layer directly adjacent the glass substrate is 600 nm or more.

* * * * *